United States Patent [19]
Thelosen et al.

[11] Patent Number: 5,680,434
[45] Date of Patent: Oct. 21, 1997

[54] X-RAY EXAMINATION APPARATUS COMPRISING A COLLIMATOR UNIT

[75] Inventors: Jacobus A. Thelosen; Johan J. Dries; Bernardus H. M. Manschot, all of Eindhoven, Netherlands

[73] Assignee: U.S. Philips Corporation, New York, N.Y.

[21] Appl. No.: 607,029

[22] Filed: Feb. 26, 1996

[30] Foreign Application Priority Data

Feb. 27, 1995 [EP] European Pat. Off. .............. 95200482

[51] Int. Cl.$^6$ .................................................. G21K 1/04
[52] U.S. Cl. ...................................... 378/150; 378/153
[58] Field of Search ................................ 378/150, 153

[56] References Cited

U.S. PATENT DOCUMENTS

| | | | |
|---|---|---|---|
| 2,295,975 | 9/1942 | Storm | 378/153 |
| 3,924,133 | 12/1975 | Reiss | 378/157 |
| 4,110,581 | 8/1978 | Meunier | 378/157 |
| 4,510,613 | 4/1985 | Caugant et al. | 378/152 |
| 4,528,685 | 7/1985 | Kump et al. | 378/157 |
| 5,235,627 | 8/1993 | Takagi | 378/151 |

FOREIGN PATENT DOCUMENTS 2053089  5/1972  Germany.

*Primary Examiner*—Craig E. Church
*Attorney, Agent, or Firm*—Jack D. Slobod

[57] ABSTRACT

An X-ray examination apparatus includes a collimator unit (4) with a diaphragm (8) for limiting the X-ray beam (2), the circular aperture (31) of the diaphragm (8) having a first diameter for a first diaphragm and a second diameter for a second diaphragm setting. The collimator unit (4) also includes an X-ray filter (20) with detachable filter elements (21).

15 Claims, 4 Drawing Sheets

X-RAY EXAMINATION APPARATUS COMPRISING A COLLIMATOR UNIT

BACKGROUND OF THE INVENTION

1. Field of the Invention

The invention relates to an X-ray examination apparatus, comprising an X-ray source for emitting an X-ray beam so as to form an X-ray image of an object, an X-ray detector for picking up the X-ray image, and a diaphragm which is arranged between the X-ray source and the X-ray detector and which has an adjustable aperture for limiting the X-ray beam, said diaphragm comprising blades which are impervious to X-rays, bound the aperture and are displaceable in a direction substantially perpendicular to the central axis of the diaphragm. The invention also relates to an X-ray examination apparatus comprising an X-ray source for emitting an X-ray beam so as to form an X-ray image of an object, an X-ray detector for picking up the X-ray image, and an X-ray filter which is arranged between the X-ray source and the X-ray detector and which comprises filter elements of different X-ray absorptivity, said filter elements being individually movable into and out of the X-ray beam.

2. Description of the Related Art

An X-ray examination apparatus of this kind is known from U.S. Pat. No. 4,528,685.

The known X-ray apparatus comprises a diaphragm for limiting the X-ray beam. The diaphragm comprises two pairs of blades which are movable perpendicularly to one another and to the central axis of the diaphragm in order to adjust the approximately rectangular aperture. It has been found that the diaphragm of the known X-ray examination apparatus does not offer adequate possibilities for influencing the cross-section of the limited X-ray beam. More specifically, it is not very well possible to make the cross-section of the X-ray beam correspond exactly to an effective X-ray-sensitive surface of the X-ray detector which is usually circular. Consequently, a substantial part of the X-rays is not used for the processing of the X-ray image and/or a part of the X-ray-sensitive surface is not used for the detection of X-rays. Either a patient to be examined in the known X-ray examination apparatus, is exposed to an X-ray dose which is higher than necessary to form the X-ray image or an X-ray image is formed whose surface area is smaller than permitted by the effective X-ray-sensitive surface area.

In an X-ray image intensifier it is possible to adjust the diameter of a substantially circular part of the surface of the entrance screen which is electron-optically imaged on the exit window. This adjustment, the so-called format setting, is realized on the basis of adjustment of an electron-optical system of the X-ray image intensifier. When an X-ray image intensifier/pick-up chain is used as the X-ray detector, therefore, the effective X-ray-sensitive surface can be adjusted, but the known X-ray apparatus does not enable accurate adjustment of the cross-section of the limited X-ray beam in conformity with the adjustment of the effective X-ray-sensitive surface.

SUMMARY OF THE INVENTION

It is an object of the invention to provide an X-ray examination apparatus comprising a diaphragm which, in comparison with the known X-ray apparatus, offers more possibilities for forming a limited X-ray beam of a cross-section which accurately corresponds to the effective X-ray-sensitive surface of the X-ray detector.

This object is achieved in an X-ray examination apparatus in accordance with the invention which is characterized in that for a first setting of the aperture the blades bound a substantially circular aperture of a first diameter and that for a second setting of the aperture the blades bound a substantially circular aperture of a second diameter.

For the first setting, the diaphragm transmits a limited X-ray beam having a substantially round cross-section of the first diameter. The limited X-ray beam accurately corresponds to a substantially circular first effective X-ray-sensitive surface of the X-ray detector, so that the effective X-ray-sensitive surface is almost completely utilized and no X-rays are lost to the formation and processing of the X-ray image. For the second setting, the diaphragm forms a limited X-ray beam having a substantially circular cross-section of the second diameter. For the second aperture setting it is achieved that substantially all X-rays of the limited X-ray beam are used for the formation and processing of the X-ray image also for a substantially circular second effective X-ray-sensitive surface of the X-ray detector.

For further settings of the aperture the blades may also bound a substantially circular aperture of a diameter other than said first and second diameters.

From German Offenlegungsschrift DE 20 530 89 it is known per se to provide an X-ray examination apparatus with a diaphragm whereby a substantially circular aperture can be adjusted for a single value of the diameter. This diaphragm, however, does not enable adaptation of the cross-section of the limited X-ray beam to the adjustment of the X-ray-sensitive surface.

A preferred embodiment of an X-ray examination apparatus in accordance with the invention is characterized in that an edge of individual blades which is intended to bound the aperture comprises a first edge portion having a first radius of curvature and a second edge portion having a second radius of curvature.

The substantially circular diaphragm aperture of the first diameter is formed by positioning the blades in such a manner that the respective first edge portions having the first radius of curvature of the individual blades adjoin one another substantially directly. In this first position the blades bound a substantially circular aperture of the first diameter which mounts to approximately twice the first radius of curvature. The substantially circular diaphragm aperture of the second diameter is formed in that the respective second edge portions of the second radius of curvature of the individual blades adjoin one another substantially directly in a second position. In the second position the blades bound a substantially circular aperture whose diameter amounts to approximately twice the second radius of curvature. The blades can be displaced over one another in such a manner that the edge portions of each blade which are not involved in bounding the aperture in one position are covered by a part of one of the other blades. The blades are preferably displaceable by rotation in a plane extending approximately transversely of the X-ray beam, so that a diaphragm occupying a comparatively small amount of space can be realised.

Furthermore, the blades may be provided with a third and possibly further edge portions of a third or possibly other radii of curvature in order to bound a substantially circular aperture having a third or other diameter.

A further preferred embodiment of an X-ray examination apparatus in accordance with the invention is characterized in that the edge of individual blades which is intended to bound the aperture comprises a third, substantially straight edge portion which is situated between said first and second edge portions.

This shape of the edge of the individual blades offers the advantage that the circular shape of the aperture is accurately approximated for the first and the second diameter and also in a range of diameter values which lies between the first and the second diameter, mainly near the largest of the first and second diameters.

A further preferred embodiment of an X-ray examination apparatus in accordance with the invention is characterized in that individual blades have the same shape and dimensions.

The manufacture and assembly of a diaphragm is simpler and hence less expensive because all blades are identical. It is not necessary to draft separate blade designs and upon assembly of the diaphragm it will not be necessary to search for appropriate blades.

A further preferred embodiment of an X-ray examination apparatus in accordance with the invention is characterized in that individual blades are consecutively arranged in the direction of the X-ray beam so as to be movable over one another in the direction perpendicular to the central axis of the diaphragm, and that positions of individual blades can be adjusted in such a manner that the edge of said blades which bounds the aperture is situated further from the center of the aperture as said blades are situated further from the X-ray source.

Because the X-ray beam diverges, an even more accurately circular cross-section of the limited X-ray beam is achieved by arranging the individual blades slightly further from the center of the diaphragm aperture as the distance between the blades and the X-ray source is slightly larger. If this embodiment is constructed by means of identical blades, a slight inaccuracy will occur because the corresponding edge portions of the individual blades have the same radius of curvature, whereas they limit a slightly larger cross-section of the X-ray beam as they are situated further from the X-ray source. Because the distance between blades is only small in comparison with their distance from the X-ray source, a sufficiently accurately circular cross-section of the limited X-ray beam is achieved despite said inaccuracy.

The invention also relates to an X-ray examination apparatus comprising an X-ray source for emitting an X-ray beam so as to form an X-ray image of an object, an X-ray detector for picking up the X-ray image, and an X-ray filter which is arranged between the X-ray source and the X-ray detector and which comprises filter elements of different X-ray absorptivity, said filter elements being individually movable into and out of the X-ray beam.

The known X-ray examination apparatus comprises an X-ray filter with separate filter elements for selecting the energy of the X-ray beam on the basis of the selection of one of the filter elements which is positioned in the X-ray beam. The individual filter elements are mounted so as to be rotatable on a holder and a selected filter element is rotated into the X-ray beam. If the set of filter elements no longer operates satisfactorily for one reason or another, the filter elements must be replaced. Replacement of the filter elements is desirable, for example, because of ageing of the filter elements or because the X-ray examination apparatus is to be used for radiological examinations other than those for which the filter elements are suitable. In order to equip the known X-ray examination apparatus with new filter elements, it is necessary to replace the entire X-ray filter; this involves complex disassembly and assembly operations.

It is a further object of the invention to provide an X-ray examination apparatus in which filter elements of an X-ray filter can be simply replaced.

This further object of the invention is achieved by means of an X-ray examination apparatus in accordance with the invention which is characterized in that the filter elements are mounted in the X-ray filter so as to be detachable.

For replacement of filter elements, the old filter elements are removed from the X-ray filter and new filter elements are arranged in the vacated positions in the X-ray filter. The X-ray filter may remain in the X-ray examination apparatus during replacement of the filter elements. For example, the X-ray filter is accommodated in a collimator unit which also comprises the diaphragm. For replacement of the filter elements it suffices to open the housing of the collimator unit, it not being necessary to remove the entire X-ray filter from the collimator unit. The replacement of filter elements involves a small number of simple disassembly and assembly operations. Therefore, the replacement of the filter elements is not time-consuming. The X-ray filter comprising detachable filter elements can be used in combination with the diaphragm or separately.

A further preferred embodiment of an X-ray examination apparatus in accordance with the invention is characterized in that the X-ray filter comprises a holder of a synthetic material in which the filter elements are clamped.

It has been found that a holder of a synthetic material can be inexpensively and readily manufactured, even when it has a complex shape. The costs of manufacturing the holder remain low notably when it is manufactured in large numbers by means of an injection-moulding process.

A further preferred embodiment of an X-ray examination apparatus in accordance with the invention is characterized in that the holder of a synthetic material is provided with a snap connection for clamping the filter elements in the holder.

A snap connection of this kind consists of, for example a more or less resilient lug with a barb-like projection. When a filter element is introduced, the lug is pushed aside and the projection subsequently clamps the filter element in the holder of a synthetic material. For removal of a filter element from the holder it suffices to push the lug slightly to the side, so that the filter element is released. A snap connection thus enables replacement of filter elements by way of only a limited number of uncomplicated operations which do not require special tools. When the holder is manufactured by means of an injection-moulding process, a snap connection can be readily realized.

These and other aspects of the invention will be apparent from and elucidated with reference to the embodiments described hereinafter.

DETAILED DESCRIPTION OF THE PREFERRED EMBODIMENTS

Figure 1:
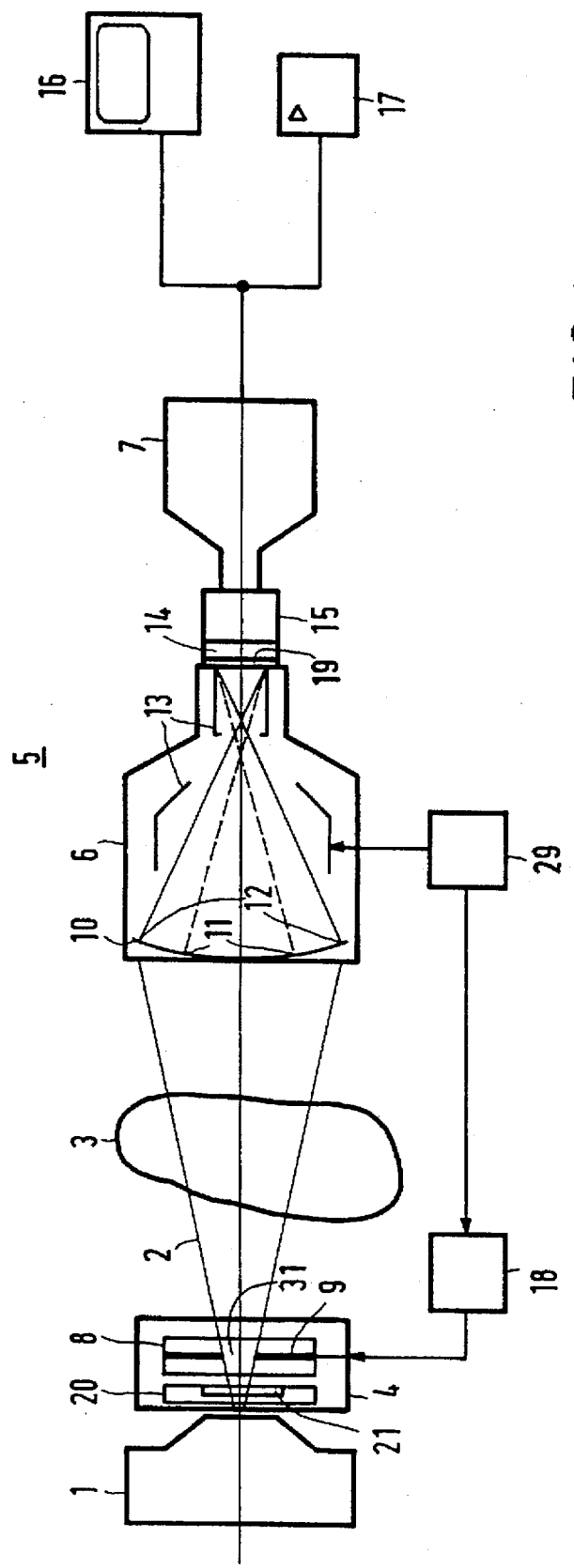
FIG. 1 shows diagrammatically an X-ray examination apparatus in accordance with the invention, comprising a diaphragm and an X-ray filter.

FIG. 1 is a diagrammatic view of an X-ray examination apparatus in accordance with the invention, comprising a collimator unit 4 with a diaphragm 8 and an X-ray filter 20. The X-ray source 1 emits an X-ray beam 2 in order to irradiate an object 3. Because of spatial variations in the X-ray absorption in the object, an X-ray image of the object, for example a patient to be examined, is formed on an X-ray-sensitive surface 11, 12 of an X-ray detector 5. The X-ray detector 5 comprises an X-ray image intensifier 6 whereto a camera 7 is optically coupled. The X-ray image intensifier comprises an entrance screen 10, an electron-optical system 13 and an exit window 14. The entrance screen converts incident X-rays into an electron beam which is conducted to the exit window 14 by the electron-optical system. The incident electrons produce an optical image on a phosphor layer 19 of the exit window 14, which optical image is picked up by the camera 7 which is coupled to the image intensifier by way of an optical coupling 15, for example a lens system. The camera 7 extracts an electronic image signal from the optical image, which image signal is applied to a monitor 16 on which the image information of the X-ray image is displayed; the electronic image signal can also be applied to an image processing unit 17 for further processing. The effective X-ray-sensitive surface 11, 12 constitutes the part of the entrance screen 10 which is electron-optically imaged on the exit window 14. Separate X-ray-sensitive surfaces of the entrance window can be adjusted on the basis of the adjustment of the electron-optical system. Various format settings can be chosen; for example, circular parts of a diameter of 23 cm (9") or 31 cm (12") of the entrance window 10 are adjusted as the effective X-ray-sensitive surface.

The X-ray examination apparatus comprises the diaphragm 8 which is arranged in front of the X-ray source so as to limit the X-ray beam. The diaphragm 8 comprises a number of blades 9 which are impervious to X-rays and which bound an aperture 31 wherethrough the limited X-ray beam is transmitted. The blades 9 are movable in the diaphragm 8, so that the aperture 31 can be adjusted in such a manner that the cross-section of the X-ray beam accurately corresponds to a part of the object or to the X-ray-sensitive surface 11, 12 of the entrance screen 10. By way of a suitable setting of the aperture of the diaphragm it is achieved that an as large a part as possible of the X-rays whereto the patient is exposed is used to form the X-ray image, the X-ray-sensitive surface of the entrance screen also being utilized as fully as possible at the same time. The diaphragm 8 comprises a control unit 18 for setting the aperture by positioning the blades 9. The X-ray examination apparatus also comprises an adjusting unit 29 for selecting the format setting by controlling the electron-optical system so as to adjust the X-ray-sensitive surface of the entrance screen 10. In order to set the diaphragm aperture in conformity with the setting of the X-ray-sensitive surface, the control unit 18 of the diaphragm is coupled to the adjusting unit 29 of the electron-optical system 13.

Figure 2:
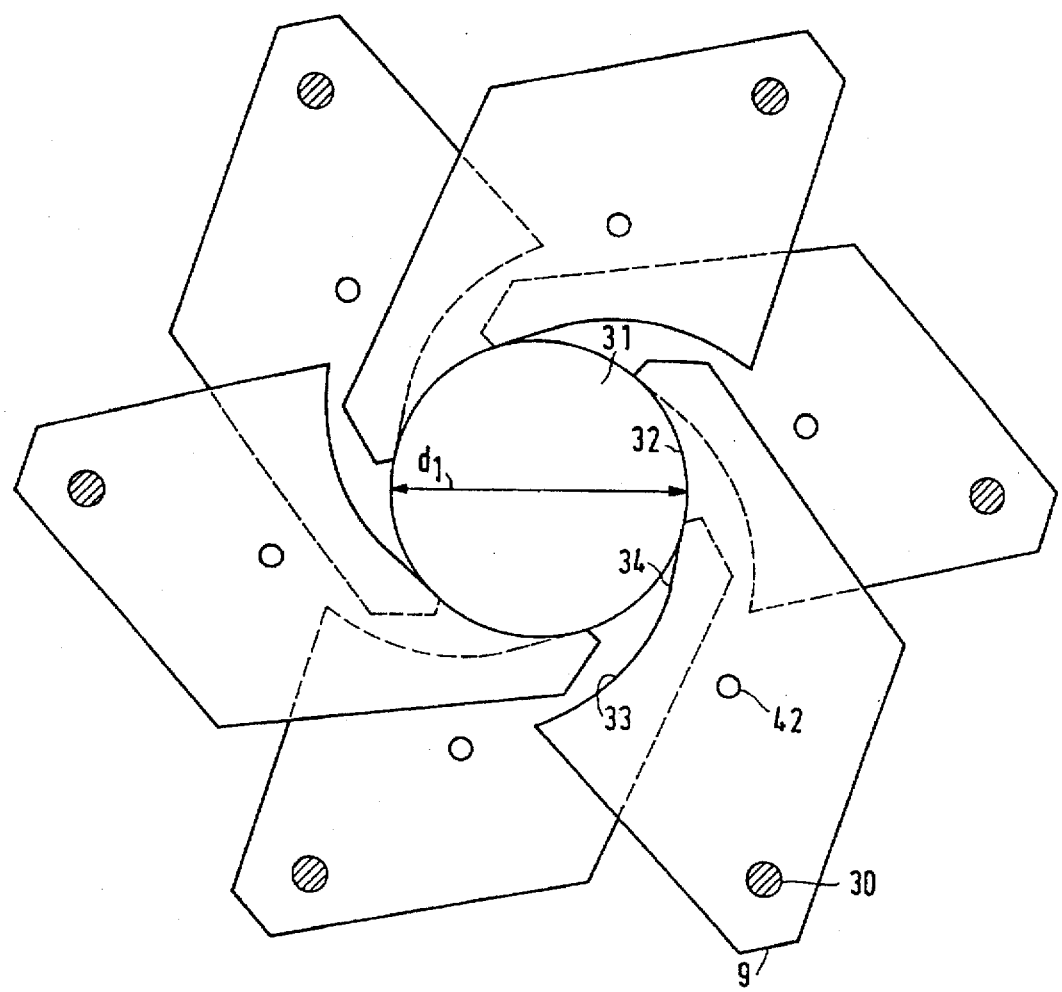
FIG. 2 is a plan view of an embodiment of a diaphragm of the X-ray examination apparatus in accordance with the invention, the aperture of the diaphragm having been adjusted to the first diameter.

FIG. 2 is a plan view of an embodiment of a diaphragm of the X-ray examination apparatus in accordance with the invention, the aperture of the diaphragm having been adjusted to the first diameter. The diaphragm comprises six blades 9, each of which is rotatable about a respective shaft 30. The blades are impervious to X-rays and bound the aperture 31 wherethrough the limited X-ray beam passes. This figure shows an aperture of the smaller of two diameters whereto it can be adjusted. For the remainder of the description it is assumed that the aperture of the first diameter is smaller than the aperture of the second diameter. The aperture shown in the drawing is bounded by successive first edge portions 32 of the blades 9. The first edge portions 32 have a first radius of curvature $R_1$ which amounts to approximately half the first diameter $d_1$. In the blade position shown, the successive first edge portions of neighbouring blades accurately adjoin one another, so that they bound a substantially circular aperture 31 of the first diameter. Rotation of the blades 9 about their respective shafts 30 results in a different position of the blades in which successive second edge portions 33 accurately adjoin one another so as to bound a substantially circular aperture of the second diameter.

Figure 3:
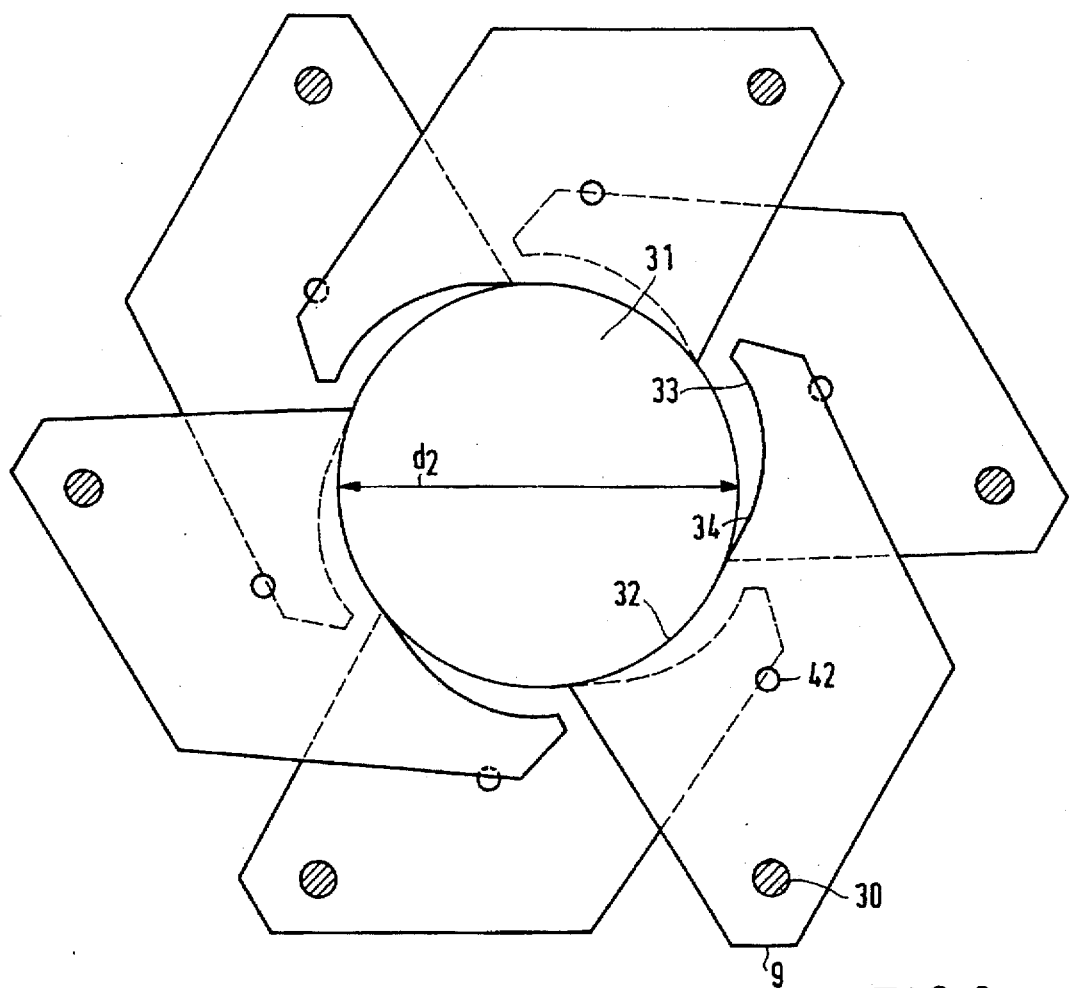
FIG. 3 is a plan view of an embodiment of a diaphragm of the X-ray examination apparatus in accordance with the invention, the aperture of the diaphragm having been adjusted to the second diameter.

FIG. 3 is a plan view of an embodiment of a diaphragm of the X-ray examination apparatus in accordance with the invention, the aperture of the diaphragm having been adjusted to the second diameter. The second edge portions of the blades have a second radius of curvature $R_2$ which amounts to approximately half the second diameter $d_2$. Each of the blades comprises a substantially straight third edge portion 34 between the first and second edge portions 32, 33. The straight edge portions ensure that a reasonably circular aperture is bounded when the blades are positioned between the positions in which a circular aperture of the first diameter and a circular aperture of the second diameter are formed. The blades are mounted on a supporting plate 35 in which a hole 36 is recessed so as to allow passage of the X-rays from the X-ray source. If desired, the hole 36 may be covered by an X-ray transparent material. Because the blades can be positioned by rotation, a comparatively compact diaphragm construction which occupies only little space, is obtained.

Figure 4:
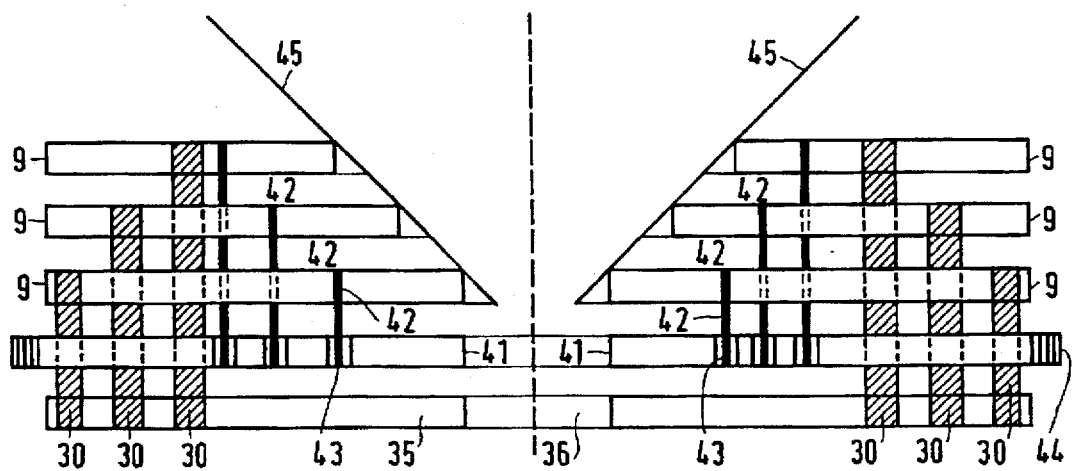
FIG. 4 is a side elevation of an embodiment of a diaphragm of the X-ray examination apparatus in accordance with the invention.

FIG. 4 is a side elevation of an embodiment of a diaphragm of the X-ray examination apparatus in accordance with the invention. The blades 9 are mounted so as to be rotatable about respective shafts 30 on the supporting plate 35. The diaphragm is provided with an adjusting ring 41 for rotation of the blades about their shafts. Each of the blades 9 comprises a pin 42 which fits in a slot or slit 43 in the adjusting ring. When the adjusting ring 41 is turned, the respective pins are taken along so that the blades are rotated about their shafts 30. Turning of the adjusting ring enables displacement of the blades between a first position in which the aperture of the first diameter is bounded and a second position in which the aperture of the second diameter is bounded. On its outer circumference the adjusting ring is provided with a gear ring 44 which is engaged by a gear wheel driven by an actuator. FIG. 4 shows that blades which are situated further from the X-ray source leave a slightly larger aperture than blades situated nearer to the X-ray source, so that the aperture of the diaphragm accurately corresponds to the divergence of the X-ray beam. This divergence is diagrammatically represented by two edge rays 45 of the X-ray beam limited by the aperture.

Figure 5:
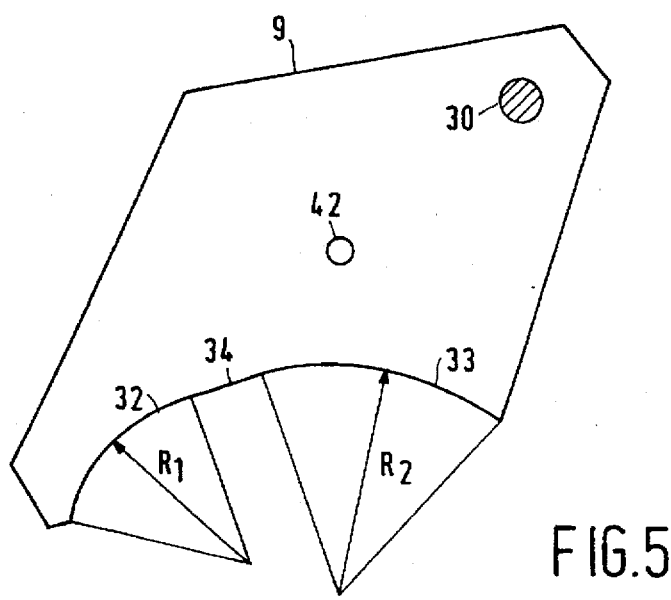
FIG. 5 is a plan view of details of one of the blades of the diaphragm shown in the FIGS. 2 and 3.

FIG. 5 is a plan view of details of one of the blades of the diaphragm shown in the FIGS. 2 and 3. The blade 9 comprises a first edge portion 32 having a first radius of curvature $R_1$ and a second edge portion 33 having a second radius of curvature $R_2$, a substantially straight third edge portion 34 being situated therebetween. In dependence on the adjusted position of the blade, the edge portions cooperate with corresponding edge portions of the other, identical blades in the diaphragm in order to bound a circular-aperture of the first or the second diameter. The blade also comprises a pin 42 whereby it is coupled to the adjusting ring 41. The blade is journalled on the shaft 30 so that it is rotated about the shaft 30 by turning of the adjusting ring. To those skilled in the art it will be evident that a suitable construction of the diaphragm is also obtained when the pins 42 are provided on the adjusting ring 41 so as to engage holes or slots in the respective blades.

Figure 6:
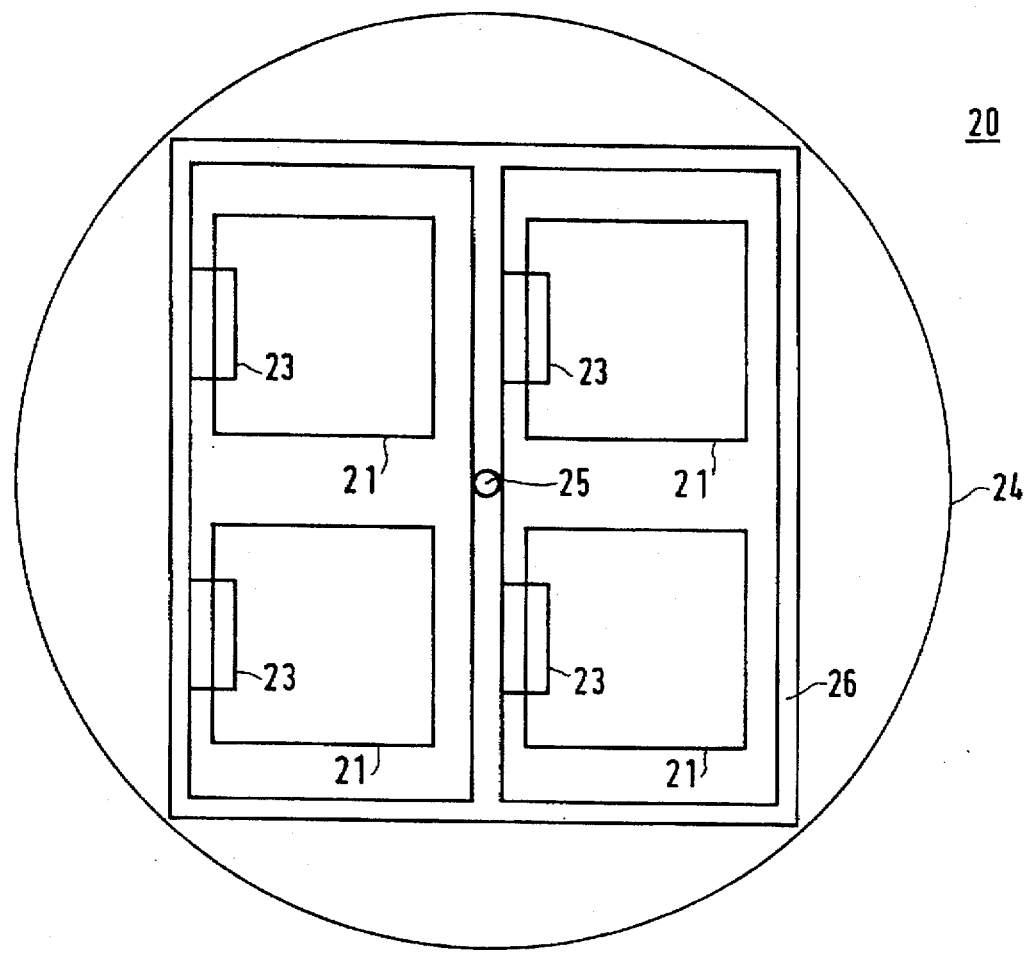
FIG. 6 is a plan view of an X-ray filter of the X-ray examination apparatus in accordance with the invention.

FIG. 6 is a plan view of an X-ray filter 20 of the X-ray examination apparatus in accordance with the invention. The individual filter elements are accommodated in a round holder 24 of a synthetic material. The X-ray filter 20 is arranged in the X-ray examination apparatus so as to be rotatable in a plane substantially perpendicular to the central ray of the X-ray beam in order to arrange one of the filter elements in the X-ray beam as desired. To this end, the axis of rotation 25 is shifted parallel to the central ray of the X-ray beam. The holder is provided with a profile 26 in which the filter elements 21 fit. The filter elements 21 are retained in the profile by way of a snap connection 23. The individual filter elements are made of different materials such as copper, aluminium or gadolinium and have different thicknesses, for example a few millimeters or approximately one centimeter, so that the filter elements have different X-ray absorptivities. The X-ray filter shown can accommodate four different filter elements. Because the X-ray filter is preferably accommodated in the collimator unit 4 together with the diaphragm in order to obtain a compact construction, the dimensions of the X-ray filter cannot be increased indefinitely. Because the filter elements can be readily exchanged in accordance with the invention, the choice of X-ray filters is larger than the four shown.

Figure 7:
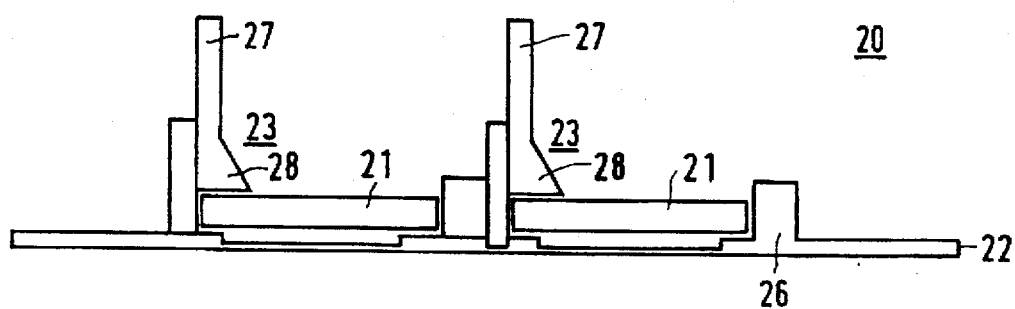
FIG. 7 is a side elevation of the X-ray filter shown in FIG. 6.

FIG. 7 is a side elevation of the X-ray filter shown in FIG. 6. The filter elements 21 fit in the profile 26 and are clamped in position by the snap connection 23 which is in this case formed by a resilient lug 27 with a barb-like projection 28. The filter element is released by pushing the lug slightly to the side, so that the substitute filter element can be arranged in the profile 26. Subsequently, the lug is released so that the substitute filter element is clamped in the profile. Because individual filter elements are replaced, it is not necessary to remove the entire X-ray filter from the collimator unit.

We claim:

1. An X-ray examination apparatus, comprising:

an X-ray source for emitting an X-ray beam so as to form an X-ray image of an object, an X-ray detector for picking up the X-ray image, and a diaphragm which is arranged between the X-ray source and the X-ray detector and which has an adjustable aperture for limiting the X-ray beam, said diaphragm comprising individual blades which are impervious to X-rays, bound the aperture and are displaceable in a direction substantially perpendicular to the central axis of the diaphragm, wherein for a first setting of the aperture the blades bound a substantially circular aperture of a first diameter, and for a second setting of the aperture the blades bound a substantially circular aperture of a second diameter, and an edge of the individual blades which is intended to bound the aperture comprises a first edge portion having a first radius of curvature, and a second edge portion having a second radius of curvature.

2. An X-ray examination apparatus as claimed in claim 1, in which the X-ray detector comprises an X-ray image intensifier which is optically coupled to a camera, and said apertures of the first and the second diameter form a limited X-ray beam whose cross-section accurately corresponds to a first part and a second part, respectively, of an entrance screen of the X-ray image intensifier which is electron-optically imaged on an exit window of the X-ray image intensifier in conformity with a format setting of the X-ray image intensifier.

3. An X-ray examination apparatus as claimed in claim 1 wherein the edge of the individual blades which is intended to bound the aperture comprises a third, substantially straight edge portion which is situated between said first and second edge portions.

4. An X-ray examination apparatus as claimed in claim 1, wherein the individual blades have the same shape and dimensions.

5. An X-ray examination apparatus as claimed in claim 1, wherein the individual blades are consecutively arranged in the direction of the X-ray beam so as to be movable over one another in the direction perpendicular to the central axis of the diaphragm, and positions of the individual blades can be adjusted in such a manner that an edge of said blades which bounds the aperture is situated further from the center of said aperture as said blades are situated further from the X-ray source.

6. An X-ray examination apparatus as claimed in claim 1, in which the X-ray detector comprises an X-ray image intensifier which is optically coupled to a camera, said apertures of the first and the second diameter form a limited X-ray beam whose cross-section accurately corresponds to a first part and a second part, respectively, of an entrance screen of the X-ray image intensifier which is electron-optically imaged on an exit window of the X-ray image intensifier in conformity with a format setting of the X-ray image intensifier.

7. An X-ray examination apparatus as claimed in claim 1, comprising an X-ray filter which is arranged between the X-ray source (1) and the X-ray detector and which comprises filter elements of different X-ray absorptivity, said filter elements being individually movable into and out of the X-ray beam, the filter elements being mounted in the X-ray filter so as to be detachable.

8. An X-ray examination apparatus as claimed in claim 5, in which the X-ray detector comprises an X-ray image intensifier which is optically coupled to a camera, and said apertures of the first and the second diameter form a limited X-ray beam whose cross-section accurately corresponds to a first part and a second part, respectively, of an entrance screen of the X-ray image intensifier which is electron-optically imaged on an exit window of the X-ray image intensifier in conformity with a format setting of the X-ray image intensifier.

9. An X-ray examination apparatus as claimed in claim 7 wherein the X-ray filter comprises a holder of a synthetic material in which the filter elements (21) are clamped.

10. An X-ray examination apparatus as claimed in claim 9, wherein the holder of a synthetic material is provided with a snap connection for clamping the filter elements in the holder.

11. An X-ray examination apparatus as claimed in claim 3, in which the X-ray detector comprises an X-ray image intensifier which is optically coupled to a camera, and said apertures of the first and the second diameter form a limited X-ray beam whose cross-section accurately corresponds to a first part and a second part, respectively, of an entrance screen of the X-ray image intensifier which is electron-optically imaged on an exit window of the X-ray image intensifier in conformity with a format setting of the X-ray image intensifier.

12. An X-ray examination apparatus as claimed in claim 3, wherein the individual blades have the same shape and dimensions.

13. An X-ray examination apparatus as claimed in claim 3, wherein the individual blades are consecutively arranged in the direction of the X-ray beam so as to be movable over one another in the direction perpendicular to the central axis of the diaphragm, and positions of the individual blades can be adjusted in such a manner that an edge of said blades which bounds the aperture is situated further from the center of said aperture as said blades are situated further from the X-ray source.

14. An X-ray examination apparatus as claimed in claim 4, wherein the individual blades are consecutively arranged in the direction of the X-ray beam so as to be movable over one another in the direction perpendicular to the central axis of the diaphragm, and positions of the individual blades can be adjusted in such a manner that an edge of said blades which bounds the aperture is situated further from the center of said aperture as said blades are situated further from the X-ray source.

15. An X-ray examination apparatus as claimed in claim 4, in which the X-ray detector comprises an X-ray image intensifier which is optically coupled to a camera, and said apertures of the first and the second diameter form a limited X-ray beam whose cross-section accurately corresponds to a first part and a second part, respectively, of an entrance screen of the X-ray image intensifier which is electron-optically imaged on an exit window of the X-ray image intensifier in conformity with a format setting of the X-ray image intensifier.

* * * * *